United States Patent
Kanai et al.

(10) Patent No.: US 11,883,831 B2
(45) Date of Patent: Jan. 30, 2024

(54) MAGNETIC PARTICLE OPERATION DEVICE

(71) Applicant: Shimadzu Corporation, Kyoto (JP)

(72) Inventors: Masaki Kanai, Kyoto (JP); Hiroyuki Jikuya, Kyoto (JP); Tetsuo Ohashi, Kyoto (JP); Seiya Fujiwara, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 1069 days.

(21) Appl. No.: 16/603,235

(22) PCT Filed: Apr. 6, 2017

(86) PCT No.: PCT/JP2017/014358
§ 371 (c)(1),
(2) Date: Jul. 27, 2020

(87) PCT Pub. No.: WO2018/185908
PCT Pub. Date: Oct. 11, 2018

(65) Prior Publication Data
US 2021/0129158 A1 May 6, 2021

(51) Int. Cl.
*B03C 1/32* (2006.01)
*C12Q 1/68* (2018.01)
(Continued)

(52) U.S. Cl.
CPC ............... *B03C 1/32* (2013.01); *B01L 3/502* (2013.01); *C12Q 1/6806* (2013.01); *G01N 35/08* (2013.01); *B01L 2400/043* (2013.01)

(58) Field of Classification Search
CPC ..... B03C 1/32; B03C 2201/18; B03C 1/0332; B03C 1/00; B03C 1/12; B03C 1/02;
(Continued)

(56) References Cited

U.S. PATENT DOCUMENTS

| 4,462,907 A * | 7/1984 | Waldecker ......... B01D 21/0009 210/223 |
| 2008/0257882 A1* | 10/2008 | Turner ................. B01L 3/50853 220/23.2 |

(Continued)

FOREIGN PATENT DOCUMENTS

| CN | 203030295 U | * | 7/2013 | ........ B01L 2400/043 |
| CN | 103269787 A | | 8/2013 | |

(Continued)

OTHER PUBLICATIONS

English Translation of Zhou Patent Publication CN203030295U, published Jul. 2013 (Year: 2013).*

(Continued)

*Primary Examiner* — Joseph W Drodge
(74) *Attorney, Agent, or Firm* — Muir Patent Law, PLLC (57) ABSTRACT

A magnetic particle operation device comprising a tubular container having a longitudinal shape and including a sample introduction space in which a sample including a target substance and magnetic particles for immobilizing the target substance thereon are received, and a sample movement space in which a gel-like medium layer and a liquid layer are alternately arranged in its longitudinal direction. The magnetic particle operation device further comprising a first magnet provided outside the tubular container to face the sample introduction space, the first magnet configured to hold the magnetic particles in the sample introduction space in the container when the device is not used; and a second magnet configured to move the magnetic particles with the target substance being immobilized thereon, from the sample introduction space to the sample movement space, passing through the gel-like medium layer and the liquid layer in the longitudinal direction, when the device is used.

7 Claims, 6 Drawing Sheets

(51) Int. Cl.
  *G01N 35/08* (2006.01)
  *B01L 3/00* (2006.01)
  *C12Q 1/6806* (2018.01)

(58) Field of Classification Search
  CPC .. B03C 1/28; B03C 1/01; B03C 1/284; B03C 1/288; G01N 35/08; G01N 35/088; G01N 35/10; G01N 2035/00564; G01N 35/0098; B01L 2400/043; B01L 3/502; B01D 35/06; B01D 12/00; B01D 29/00; C12Q 1/6806; B01J 19/08
  USPC .......................... 210/695, 223; 209/223, 224
  See application file for complete search history.

(56) References Cited

U.S. PATENT DOCUMENTS

2013/0273552 A1  10/2013  Ohashi
2018/0112207 A1   4/2018  Kanai et al.

FOREIGN PATENT DOCUMENTS

WO   WO-1994011075 A1 *  5/1994  ............. B01B 35/06
WO      2012-086243 A1    6/2012
WO      2016-113883 A1    7/2016

OTHER PUBLICATIONS

Written Opinion of the International Searching Authority for International Application PCT/JP2017/014358 dated Jun. 27, 2017 with partial, machine, English translation.

Office Action from the Chinese Intellectual Property Office dated Dec. 23, 2020, for corresponding application No. CN 201780087798.X.

Office Action from the Chinese Intellectual Property Office for corresponding application No. CN 201780087798.X, dated Dec. 16, 2021, submitted with a machine translation.

* cited by examiner

MAGNETIC PARTICLE OPERATION DEVICE

TECHNICAL FIELD

The present invention relates to a magnetic particle operation device provided with a tubular container in which an inner space in which a gel-like medium layer and a liquid layer are alternately layered in its longitudinal direction in which magnetic particles are provided is formed.

BACKGROUND ART

In a medical examination, a food safety and hygiene management, environmental monitoring, etc., it is required to extract a target substance from a sample containing a wide variety of impurities and use it for detection and/or reaction. For example, in a medical examination, it is necessary to detect, identify, and quantify nucleic acids, proteins, sugars, lipids, bacteria, viruses, radioactive substances, etc., contained in blood, serum, cells, urine, stool, etc., isolated and obtained from animals and plants. In these examinations, in sometimes, it is necessary to separate and purify the target substance in order to eliminate adverse effects such as background caused by impurities.

To separate and purify a target substance in a sample, a method has been developed and put into practical use in which magnetic particles having a chemical affinity for a target substance or a molecular recognition function on a surface of a magnetic body having a particle diameter of about 0.5 m to several tens of μm are used. In this method, a step is repeated in which after immobilizing the target substance on the surface of the magnetic particles, the magnetic particles are separated and collected from a liquid phase by a magnetic field operation, and if necessary, the collected magnetic particles are dispersed in a liquid phase, such as, e.g., a cleaning fluid, and the magnetic particles are separated and collected from the liquid phase. Thereafter, the magnetic particles are dispersed in an eluent, so that the target substance immobilized to the magnetic particles is released into the eluate, and the target substance in the eluate is collected. By using magnetic particles, the target substance can be collected by a magnet, which is advantageous for automation of chemical extraction and/or purification.

As a method for separating or purifying such a target substance, a method using a tubular container such as a capillary has been proposed (for example, see Patent Document 1 below).

In the method described in Patent Document 1, a liquid layer of a dissolving/immobilizing solution, a cleaning fluid, an eluate, etc., and a gel-like medium layer are alternately layered in a tubular container (tubular device) such as a capillary. Then, after introducing magnetic particles and a sample into the tubular device, a magnetic field applying means, such as, e.g., a permanent magnet, is brought close to the tubular device. Thereafter, the magnetic substance applying means is moved along the longitudinal direction of the tubular device to move the magnetic particles so as to follow the magnetic field applying means, thereby separating or purifying the target substance.

PRIOR ART DOCUMENT

Patent Document
Patent Document 1: International Patent Publication No. WO2012/086243

SUMMARY OF THE INVENTION

Problems to be Solved by the Invention

In the process of separating or purifying a target substance in a sample as described above, an operator usually mixes magnetic particles and a sample outside a tubular device, and introduces this mixture (mixed solution) into the tubular device. For this reason, it is necessary to prepare a container for mixing the magnetic particles and the sample, and it is also necessary to separately perform a mixing operation. This causes the operation to be complicated.

In light of the above, it could be envisaged that magnetic particles are provided in advance in a liquid layer (uppermost liquid layer) in a tubular device, and a sample is introduced into the tubular device when used. With this, preparation of a mixing container and a mixing operation can be omitted. In the case of using such a method, it is necessary to store the tubular device in a state in which magnetic particles are introduced in the tubular device. However, if the tubular device is stored in a state in which magnetic particles are introduced in the tubular device, some of the magnetic particles in the liquid layer are brought into contact with the surface of the gel-like medium layer or buried in the gel-like medium layer by their own weights. Such magnetic particles in contact with the gel-like medium layer remain held by the gel-like medium layer at the time of using the tubular device, so that the magnetic particles cannot immobilize the target substance on the surface. That is, the magnetic particles in contact with the gel-like medium layer cannot contribute to the separation/purification of the target substance at the time of using the tubular device.

The present invention has been made in view of the aforementioned circumstances, and aims to provide a magnetic particle operation device capable of simplifying an operation of an operator and suppressing generation of magnetic particles which do not contribute to separation/purification of a target substance.

Means for Solving the Problems (1) A magnetic particle operation device according to the present invention is provided with a tubular container in which an inner space in which a gel-like medium layer and a liquid layer are alternately layered in its longitudinal direction in which magnetic particles are provided is formed. The container is provided therein with a sample introduction space in which liquid holding the magnetic particles is provided and a sample is introduced and a sample movement space in which the gel-like medium layer and the liquid layer are alternately layered in the longitudinal direction and a target component included in the sample in the sample introduction space is moved in the longitudinal direction with the target component immobilized to the magnetic particles. A magnet is arranged in contact with or close to an outside of the sample introduction space in the container.

According to such a configuration, during the storage of the magnetic particle operation device, the magnetic particles in the sample introduction space are aggregated and held at the position facing the magnet in the sample introduction space by the magnetic force of the magnet.

Therefore, it is possible to prevent the magnetic particles from coming into contact with the gel-like medium layer during the storage of the magnetic particle operation device.

Further, when using the magnetic particle operation device, the magnetic particles can be dispersed in the liquid layer by moving the magnet away from the container. By introducing a sample in the magnetic particle operation device in this state, the sample and the magnetic particles can be smoothly mixed in the liquid layer in the sample introduction space. Thus, the target substance can be immobilized to the magnetic particles.

For this reason, a series of operations of mixing magnetic particles and a sample outside the magnetic particle operation device and introducing the mixture (mixed solution) into the magnetic particle operation device can be omitted. Further, the magnetic particles are not brought into contact with the gel-like medium layer during the storage, so almost all of the magnetic particles can be used for separation/purification of the target substance.

As described above, according to the magnetic particle operation device of the present invention, the operation of the operator can be simplified and the generation of magnetic particles which do not contribute to the separation/purification of the target substance can be suppressed.

(2) Further, a recess may be formed on an inner surface of the container where the sample introduction space is located to face the magnet.

According to such a configuration, the magnetic particles in the sample introduction space are aggregated at the inner side of the recess formed on the inner surface of the container by the magnetic force of the magnet.

Therefore, the magnetic particles can be held by the container recess.

As a result, the magnetic particles can be stably held in the liquid layer during the storage of the magnetic particle operation device.

(3) Further, in the container, an opposing surface for moving a magnetic field application unit in the longitudinal direction with the magnetic field application unit opposed to the opposing surface may be formed. The recess may be formed at a position different from a side of the opposing surface on the inner surface of the container.

According to such a configuration, when the magnetic field application unit is moved along the container, it is possible to prevent the recess of the container from becoming an obstacle to the movement of the magnetic field application unit.

Further, after the magnetic particles are dispersed in the liquid layer, the magnetic particles can be separated from the recess of the container by the magnetic force of the magnetic field application unit.

Therefore, when the magnetic field application unit is moved along the container, it is possible to suppress the magnetic particles from remaining in the recess of the container.

(4) Further, the magnet may be arranged in contact with or close to the container at a position lower than a liquid level of the liquid in the sample introduction space.

According to such a configuration, the magnetic particles can be held in the liquid layer during the storage of the magnetic particle operation device.

Therefore, it is possible to prevent the magnetic particles from being exposed to the outside of the liquid layer to be dried during the storage of the magnetic particle operation device.

(5) Further, the magnet may be detachably attached to the outside of the sample introduction space in the container.

According to such a configuration, by attaching the magnet to the container, the magnetic particles can be held in the liquid layer of the container by the magnetic force of the magnet. Then, by separating the magnet from the container, the magnetic particles can be dispersed in the liquid layer.

(6) Further, the magnet may be attached by a sealing member adhered to the container.

According to such a configuration, the magnet can be attached to and detached from the container with a simple configuration.

(7) Further, the container may be provided with a main body and a cap. In the main body, the sample introduction space and the sample movement space are formed. The cap is detachably attached to the main body to open and close the sample introduction space. The sealing member may be adhered so as to cross the main body and the cap.

According to such a configuration, when an operator performs an operation of removing the sealing member in order to remove the cap from the container, the magnet is detached from the container along with the operation.

Therefore, a series of operations for separating the magnet from the container can be simplified.

Effects of the Invention

According to the present invention, the magnetic particles in the sample introduction space are aggregated and held at a position facing the magnet in the sample introduction space by the magnetic force of the magnet. Therefore, during the storage of the magnetic particle operation device, the magnetic particles can be prevented from being brought into contact with the gel-like medium layer, and almost all of the magnetic particles can be used for separation/purification of the target substance. Further, when using the magnetic particle operation device, the magnetic particles can be dispersed in the liquid layer by moving the magnet away from the container. As described above, according to the magnetic particle operation device of the present invention, the operation of the operator can be simplified and generation of magnetic particles which do not contribute to the separation/purification of the target substance can be suppressed.

EMBODIMENT FOR CARRYING OUT THE INVENTION

Figure 1:
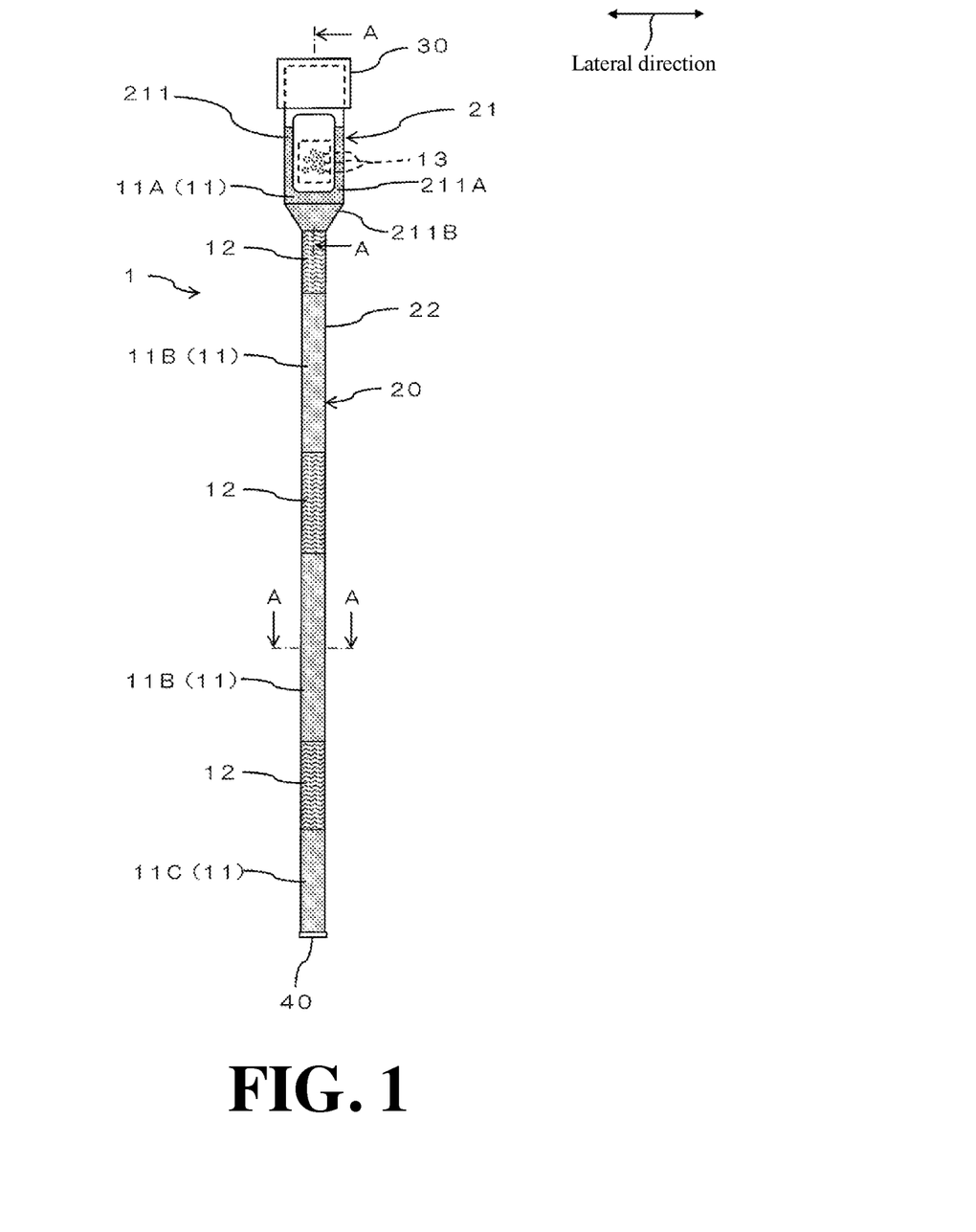
FIG. 1 is a front view showing a configuration example of a magnetic particle operation device according to a first embodiment of the present invention.

1. Configuration of Magnetic Particle Operation Device
(1) Internal Configuration of Magnetic Particle Operation Device FIG. 1 is a front view showing a configuration example of a magnetic particle operation device 1 according to a first embodiment of the present invention. The magnetic particle operation device 1 (hereinafter referred to as "device 1") is for extracting/purifying a target substance from a liquid sample, and is provided with a tubular container 20 extending straightly.

In the container 20, a plurality of liquid layers 11 and a plurality of gel-like medium layers 12 are formed. Specifically, the liquid layer 11 is formed at the lowermost portion of the container 20, and a gel-like medium layer 12 and a liquid layer 11 are alternately layered as it advances upward in the longitudinal direction. In this example, four liquid layers 11 and three gel-like medium layers 12 are alternately formed in the longitudinal direction (up-down direction), but not limited to. The number of liquid layers 11 and gel-like medium layers 12 may be arbitrarily set.

The uppermost liquid layer 11 in the container 20 is a liquid sample containing a target substance, and a large number of magnetic particles 13 are provided as will be described later. The uppermost liquid layer 11 in the container 20 is an immobilization layer 11A for immobilizing the target substance to the magnetic particles 13. The lowermost liquid layer 11 in the container 20 is an eluting layer 11C for eluting the target substance in the liquid sample. One or a plurality (two in this example) of the liquid layers 11 in the middle part of the container 20 are cleaning layers 11B for removing impurities contained in the liquid sample. These liquid layers 11 are separated from each other by a gel-like medium layer 12. In a state in which the target substance contained in the liquid sample is immobilized to the magnetic particles 13 in the immobilization layer 11A, an operation (particle operation) of moving the magnetic particles 13 from the uppermost portion to the lowermost portion of the container 20 by changing the magnetic field is performed. During the operation, the target substance is cleaned by the cleaning layers 11B and then eluted into the lowermost eluting layer 11C.

The magnetic particles 13 are particles capable of specifically immobilizing a target substance, such as, e.g., nucleic acids and antigens, to the surface or inside thereof. By dispersing the magnetic particles 13 in the uppermost liquid layer 11 (immobilization layer 11A) of the container 20, the target substance contained in the liquid layer 11 is selectively immobilized to the magnetic particles 13.

In cases where the target substance is contained in a cell of a biological sample, a solution for cell lysis is sealed in the immobilization layer 11A. For example, in cases where a nucleic acid in a blood sample is used as a target substance, it is preferable that a chaotropic agent is contained in the immobilization layer 11A.

The method for immobilizing the target substance to the magnetic particles 13 is not particularly limited, and various known immobilizing mechanisms, such as, e.g., physical adsorption and chemical adsorption, can be applied. For example, the target substance is immobilized to the surface or the inside of the magnetic particles 13 by various intermolecular forces, such as, e.g., van der Waals force, hydrogen bond, hydrophobic interaction, ion-ion interaction, and π-π stacking.

The particle diameter of the magnetic particle 13 is preferably 1 mm or less, more preferably 0.1 µm to 500 µm, and even more preferably 3 µm to 5 µm. The shape of the magnetic particle 13 is preferably a spherical shape with uniform particle diameters, but may be an irregular shape and have a certain degree of particle diameter distribution as long as the particle operation is possible. The constituent component of the magnetic particles 13 may be composed of a single substance or may be composed of a plurality of components.

The magnetic particle 13 may be composed only of a magnetic body, but those having a coating for specifically immobilizing the target substance to the surface of the magnetic body is preferably used. Examples of the magnetic body include iron, cobalt, nickel, and their compounds, oxides, and alloys. Specific examples include magnetite ($Fe_3O_4$), hematite ($Fe_2O_3$ or $\alpha Fe_2O_3$), maghemite ($\gamma Fe_2O_3$), titanomagnetite ($xFe_2TiO_4 \cdot (1-x)\ Fe_3O_4$), ilmenohegmatite ($xFeTiO_3 \cdot (1-x)\ Fe_2O_3$), pilotite ($Fe1-xS$ (x=0 to 0.13) ... $Fe_7S_8$ (x to 0.13)), grayite ($Fe_3S_4$), goethite ($\alpha FeOOH$), chromium oxide ($CrO_2$), permalloy, arconi magnet, stainless steel, samarium magnet, neodymium magnet, and barium magnet.

Examples of the target substance which is to be selectively immobilized to the magnetic particles 13 include biological substances, such as, e.g., nucleic acid, proteins, sugars, lipids, antibodies, receptors, antigens, and ligands, and cells themselves. When the target substance is a biological substance, the target substance may be immobilized to the inside of the magnetic particles 13 or the particle surface by molecular recognition or the like. For example, when the target substance is nucleic acid, magnetic particles each having a silica coating on the surface are preferably used as the magnetic particles 13. When the target substance is an antibody (e.g., a labeled antibody), a receptor, an antigen, a ligand, etc., the target substance can be selectively immobilized to the particle surface by amino groups, carboxyl groups, epoxy groups, apidine, piotine, digoxigenin, protein A, protein G, etc., to the surface of the magnetic particles 13. As the magnetic particles 13 capable of selectively immobilizing a specific target substance, for example, commercial products, such as, e.g., Dynabeads (registered trademark) sold by Life Technologies, Inc. and MagExtractor (registered trademark) sold by Toyobo Co., Ltd., can also be used.

When the target substance is nucleic acid, the cleaning fluid (cleaning layer 11B) may be a fluid capable of separating a component other than the nucleic acid contained in the liquid sample (e.g., protein, carbohydrate, etc.), or reagents used for nucleic acid extraction, etc., into the cleaning fluid while maintaining the state in which the nucleic acid is immobilized to the surface of the magnetic particles 13. Examples of the cleaning fluid (cleaning layer 11B) include a high salt concentration aqueous solution, such as, e.g., sodium chloride, potassium chloride, and ammonium sulfate, and an alcohol aqueous solution, such as, e.g., ethanol and isopropanol.

As an eluate (eluting layer 11C) for eluting nucleic acid, water or a buffer solution containing a low-concentration salt may be used. Specifically, a Tris buffer solution, a phosphate buffer solution, distilled water, etc., may be used, and it is common to use 5 mM to 20 mM Tris buffer solution adjusted to pH 7 to pH9. By dispersing the magnetic particles 13 to which nucleic acid is immobilized in the eluate, it is possible to separate and elute the nucleic acid into the nucleic acid eluate. The collected nucleic acid may be subjected to operations, such as, e.g., concentration and drying, as necessary, and then subjected to an analysis, a reaction, and the like.

The gel-like medium layer 12 is in a gel state or in a paste state before the particle operation. The gel-like medium layer 12 is preferably made of a substance having insolubility or poor solubility to the adjacent liquid layer 11 and is chemically inert. Here, having insolubility or poor solubility to liquid means that the solubility to liquid at 25° C. is about 100 ppm or less. The chemically inert substance refers to a substance that does not exert a chemical effect on the liquid layer 11, the magnetic particles 13, and the substance immobilized to the magnetic particles 13 due to the contact with the liquid layer 11 and the operation of the magnetic particles 13 (that is, the operation of moving the magnetic particles 13 in the gel-like medium layer 12).

The material and composition of the gel-like medium layer 12 are not particularly limited, and may be a physical gel or a chemical gel. For example, as described in WO2012/086243, a physical gel is formed by heating a water-insoluble or poorly water-soluble liquid substance, adding a gelling agent to the heated liquid substance, completely dissolving the gelling agent, and then cooling them to the sol-gel transition temperature or below.

(2) Shape of Container of Magnetic Particle Operation Device

The container 20 of the device 1 is a tubular container formed linearly. As will be described in detail later, the container 20 is normally used in a state in which its longitudinal direction is along the up-down direction. The container 20 is provided with a bulging portion 21 and a straight portion 22.

The bulging portion 21 is provided at the uppermost portion of the container 20. The bulging portion 21 has an inner diameter and an outer diameter larger than those of other portions. The upper surface of the bulging portion 21 is served as an opening portion, and the opening portion can be sealed with a cap 30 capable of being attached to and detached from the bulging portion 21. The inner space of the bulging portion 21 is an example of a sample introduction space. That is, the cap 30 is for opening and closing the sample introduction space. In the bulging portion 21, the liquid layer 11 (immobilization layer 11A) described above is provided. The detailed configuration of the bulging portion 21 will be described later.

The straight portion 22 is arranged below the bulging portion 21. The straight portion 22 is formed in a cylindrical shape extending in the up-down direction, and extends (linearly) while keeping the shape from the upper end to the lower end. Although not illustrated, the rear surface of the straight portion 22 is formed in a flat surface shape along the width direction that is a direction orthogonal to the front-rear direction and the up-down direction, and extends in the up-down direction. That is, the rear surface of the straight portion 22 is formed flush. In the straight portion 22, the above-described cleaning layer 11B, eluting layer 11C, and gel-like medium layer 12 are provided. Specifically, in the straight portion 22, the cleaning layer 11B and the gel-like medium layer 12 are alternately provided in the up-down direction, and the eluting layer 11C is provided below them. The uppermost gel-like medium layer 12 is arranged below the immobilization layer 11A of the bulging portion 21 and is adjacent to the immobilization layer 11A. Under the lowermost gel-like medium layer 12, the eluting layer 11C is arranged, and the gel-like medium layer 12 and the eluting layer 11C are adjacent to each other. In this example, in the straight portion 22, two cleaning layers 11B, one eluting layer 11C, and three gel-like medium layers 12 are arranged.

An opening is formed at the lower end of the straight portion 22 (the bottom surface of the container 20), and the opening is sealed with a film member 40. The target substance eluted in the eluate which is the lowermost liquid layer 11 (eluting layer 11C) in the straight portion 22 can be sucked into a pipette by inserting the pipette into the eluate so as to penetrate the film member 40. The film member 40 is formed of, for example, aluminum, but is not limited thereto. The inner space of the straight portion 22 is an example of a sample movement space.

The process of providing the liquid layers 11 and the gel-like medium layers 12 into the container 20 may be performed by an appropriate method. In cases where the tubular container 20 is used as in this embodiment, prior to the process of providing, it is preferable that the opening at one end (for example, the lower end) of the container 20 be sealed and the liquid layer 11 and the gel-like medium layer 12 be sequentially provided from the opening portion at the other end (for example, the upper end).

The capacity of each portion in the container 20, that is, the capacity of each of the liquid layer 11 and the gel-like medium layer 12 provided in the container 20 may be appropriately set according to the amount of magnetic particles 13 to be operated, the type of operation, and the like.

In cases where a plurality of liquid layers 11 and a plurality of gel-like medium layers 12 are provided in the container 20 like in this embodiment, the capacity of each portion (each layer) may be the same or different. The thickness of each portion (each layer) may also be set appropriately. When considering the operability, etc., the thickness of each portion (each layer) is preferably about 2 mm to about 20 mm, for example.

Although the thickness of the container 20 is not particularly limited, when the wall thickness is constant on the rear side opposed to the operation magnet 130 (described later), the distance between the operation magnet 130 and the inner peripheral surface of the container 20 can be kept constant, so that the magnetic particles 13 can be moved smoothly. For this reason, it is preferable that the thickness of the container 20 be constant on the rear side at least at the portion where the gel-like medium layer 12 is provided. The length of the container 20 is not particularly limited, and may be about 50 mm to about 200 mm as an example.

The material of the container 20 is not particularly limited as long as it can move the magnetic particles 13 in the container 20 and can hold the liquid layer 11 and the gel-like medium layer 12. In order to move the magnetic particles 13 in the container 20 by changing the magnetic field from the outside of the container 20 (magnetic field operation), a magnetically permeable material, such as, e.g., plastic, is preferable, and examples thereof include a resin material, such as, e.g., polyolefin such as polypropylene and polyethylene, fluorine-based resin such as tetrafluoroethylene, polyvinyl chloride, polystyrene, polycarbonate, and cyclic polyolefin. As the material of the container 20, ceramics, glass, silicone, non-magnetic metal, etc., may be used in addition to the above-mentioned materials. In order to increase the water repellency of the inner wall surface of the container 20, coating with a fluorine resin, silicone, or the like may be performed.

(3) Detailed Configuration of Bulging Portion and Surrounding Members

Figure 2:
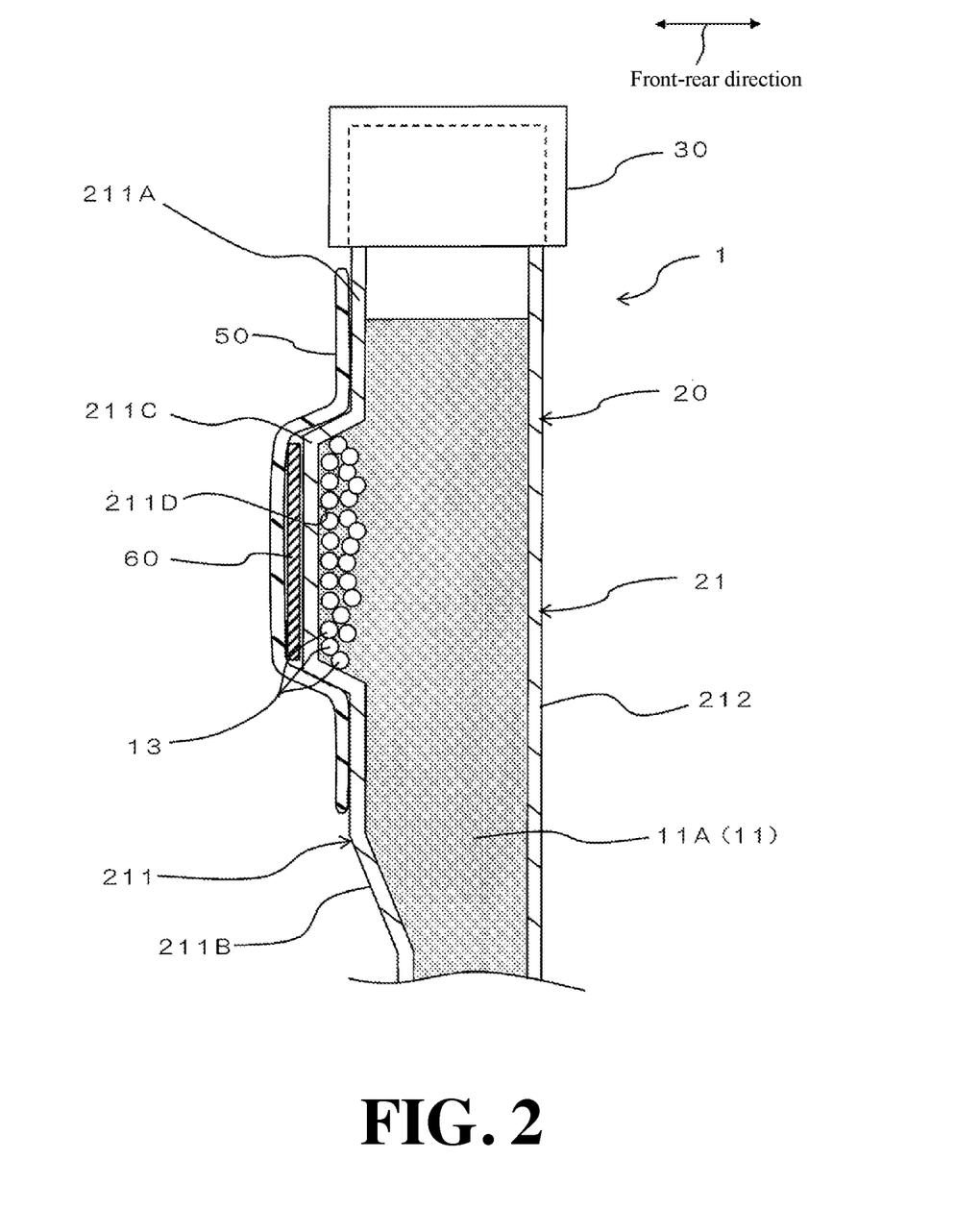
FIG. 2 is a cross-sectional view taken along the line A-A of the magnetic particle operation device in FIG. 1.

FIG. 2 is a cross-sectional view of the magnetic particle operation device 1 taken along the line A-A.

In the device 1, the bulging portion 21 is formed in a cylindrical shape extending in the up-down direction. The front surface 211 of the bulging portion 21 includes a vertical surface 211A and a tapered surface 211B. The rear surface 212 of the bulging portion 21 is formed in a flat shape along the width direction and extends in the up-down direction. That is, the rear surface 212 of the bulging portion 21 is formed flush. The rear surface 212 of the bulging portion 21 is an example of an opposing surface.

The vertical plane 211A is an upper portion and a center portion of the front surface 211 and extends in the up-down direction. At the vertical plane 211A, a protruding portion 211C is formed.

The protruding portion 211C protrudes forward from the vertical plane 211A. The protruding portion 211C is formed in a trapezoidal shape when viewed from the side. With this, a recess 211D recessed forward is formed on the inner surface (rear side surface) of the protruding portion 211C. As described above, the recess 211D is formed at a position different from the rear surface 212 and opposed to the rear surface 212. The upper end portion of the recess 211D is inclined so as to go forward as it goes downward, and the lower end portion of the recess 211D is inclined so as to go backward as it goes downward.

The tapered surface 211B is a lower portion of the front surface 211 and is arranged below the vertical plane 211A. The tapered surface 211B is continuous with the lower end of the vertical plane 211A and is inclined toward the rear side as it goes downward.

A sealing member 50 is adhered to the vertical plane 211A of the bulging portion 21. The sealing member 50 covers the entire protruding portion 211C of the vertical plane 211A. A holding magnet 60 is interposed between the sealing member 50 and the protruding portion 211C. That is, the holding magnet 60 is attached to the outside of the bulging portion 21 (container 20) by the sealing member 50 adhered to the vertical plane 211A.

The holding magnet 60 is a permanent magnet and is formed in a flat plate shape. The holding magnet 60 is in contact with the protruding portion 211C so as to substantially cover the front side surface of the protruding portion 211C. That is, the holding magnet 60 is opposed to the recess 211D.

Inside the bulging portion 21, as described above, the liquid layer 11 (immobilization layer 11A) is provided, and a large number of magnetic particles 13 are also provided. The holding magnet 60 is arranged at a position lower than the liquid level of the liquid layer 11 (immobilization layer 11A) in the bulging portion 21. The magnetic particles 13 are aggregated in the recess 211D of the bulging portion 21 in the liquid layer 11 (immobilization layer 11A) by the magnetic force of the holding magnet 60.

As described above, in the device 1, the holding magnet 60 is arranged outside the bulging portion 21 (protruding portion 211C), and the magnetic particles 13 in the bulging portion 21 are aggregated in the recess 211D by the magnetic force of the holding magnet 60. The device 1 is stored in this state. That is, the device 1 is stored in a state in which the magnetic particles 13 are introduced therein and the magnetic particles 13 are held at a fixed position (recess 211D) in the uppermost liquid layer 11 (immobilization layer 11A).

2. Magnetic Particle Operation Device

Figure 3:
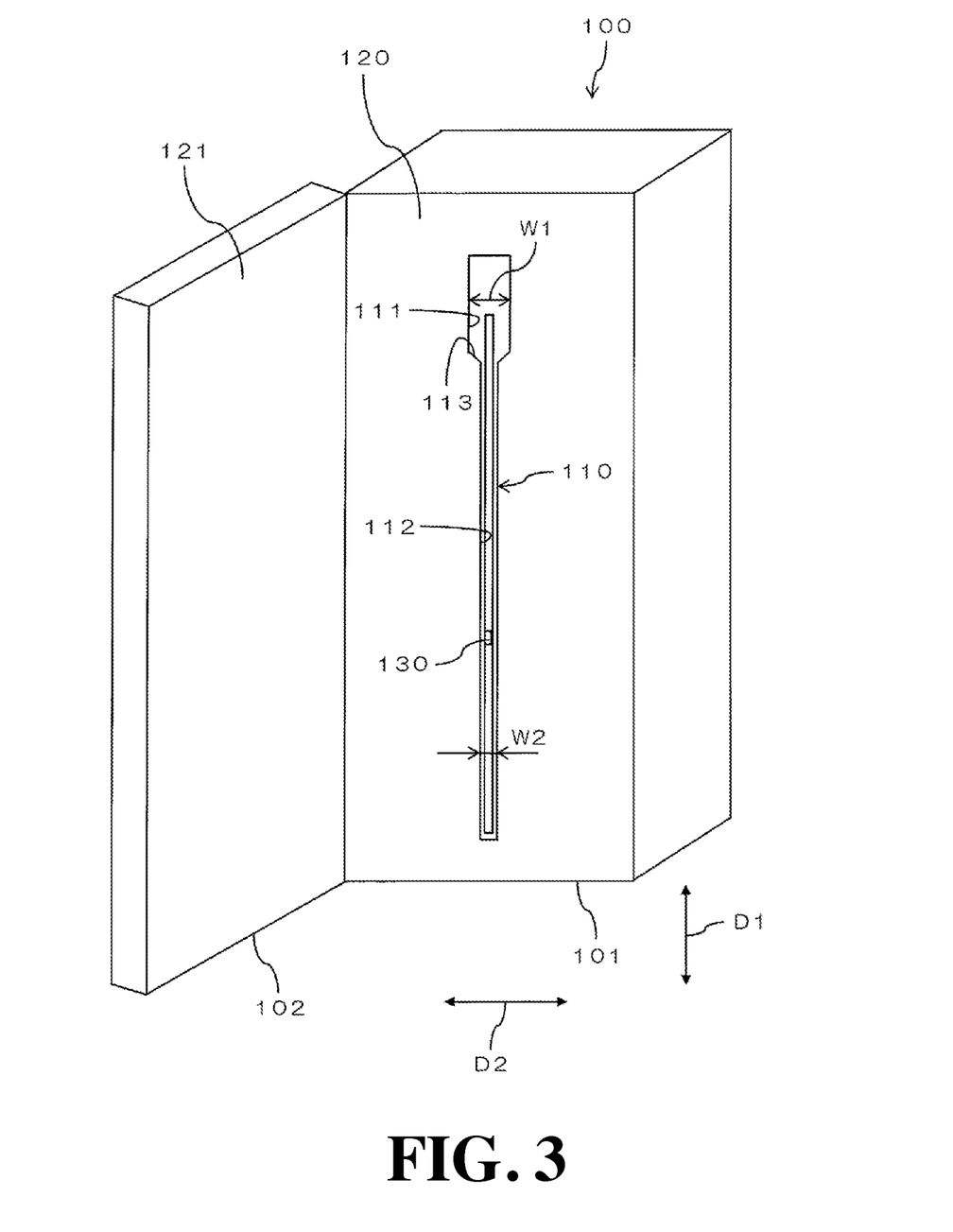
FIG. 3 is a front view showing a configuration example of a magnetic particle operation apparatus.

FIG. 3 is a front view showing a configuration example of a magnetic particle operation apparatus 100. This magnetic particle operation apparatus 100 (hereinafter referred to as "apparatus 100") is a device configured to be used in a state in which the device 1 shown in FIG. 1 and FIG. 2 is fixed to perform a particle operation on the target substance contained in the liquid sample in the container 20 of the device 1.

The apparatus 100 is provided with a main body 101 in which a container holding portion 110 for holding the device 1 is formed and a container pressing portion 102 for pressing to fix the container 20 of the device 1 held in the container holding portion. In this example, the container pressing portion 102 is constituted by a door pivotally attached to the main body 101 by a hinge (not illustrated). However, the container pressing portion 102 is not limited to a configuration capable of rotating with respect to the main body 101, but may be a configuration capable of being slidable with respect to the main body 101 or a configuration capable of being detachable with respect to the main body 101 as long as the device 1 held in the container holding portion 110 can be fixed.

The container holding portion 110 is configured by a recess formed on the front surface 120 of the main body 101. The container holding portion 110 is formed so that a first accommodation portion 111 for accommodating the bulging portion 21 of the device 1 and a second accommodation portion 112 for accommodating the straight portion 22 of the device 1 extend continuously in the up-down direction D1. Further, the width of the container holding portion 110 in the lateral direction D2 orthogonal to the direction in which the container 20 extends (up-down direction D1) and parallel to the front surface 120 of the main body 101 is a width corresponding to the device 1.

Specifically, the width W1 of the first accommodation portion 111 in the lateral direction D2 is slightly larger than the width of the bulging portion 21 of the device 1. On the other hand, the width W2 of the second accommodation portion 112 in the lateral direction D2 is slightly larger than the width of the straight portion 22 of the device 1 and smaller than the width of the bulging portion 21. Further, the first accommodation portion 111 and the second accommodation portion 112 are connected by a drawn portion 113 inclined with respect to the up-down direction D1. With this, in a state in which the device 1 is accommodated in the container holding portion 110, the bulging portion 21 of the device 1 is caught by the drawn portion 113 of the container holding portion 110 and is held in a suspended state.

Although not illustrated the device 1 is accommodated in the container holding portion 110 such that the longitudinal direction is along the up-down direction, the front surface (the front surface 211 of the bulging portion 21 and the front surface of the straight portion) face forward, the rear surface (the rear surface 212 of the bulging portion 21 and the rear surface of the straight portion 22) faces rearward.

In this state, by closing the door constituting the container pressing portion 102, the device 1 is fixed in the apparatus 100.

The container holding portion 110 has an opening on the rear surface side, and an operation magnet 130 is arranged so as to face the container holding portion 110. The operation magnet 130 is a permanent magnet, and is held slidably along the up-down direction D1. The operation magnet 130 attracts the magnetic particles 13 dispersed in the device 1 (container 20) with a magnetic force. With this, the magnetic particles 13 dispersed in the container 20 are collected on the rear surface side of the container 20. The magnetic particles 13 in the container 20 can be moved in the up-down direction D1 by moving the operation magnet 130 in the up-down direction D1 with the magnetic particles 13 attracted on a side of the operation magnet 130.

In this way, the operation magnet 130 constitutes a magnetic field application unit that moves the magnetic particles 13 in the container 20 by changing the magnetic field. The operation magnet 130 may be slid by a driving means such as a motor, or may be slid manually. As the magnetic force source of the magnetic field application unit, other than the operation magnet 130, an electric magnet may be used. The magnetic field application unit may have a plurality of magnetic force sources.

3. Operation of Magnetic Particles

Figure 4:
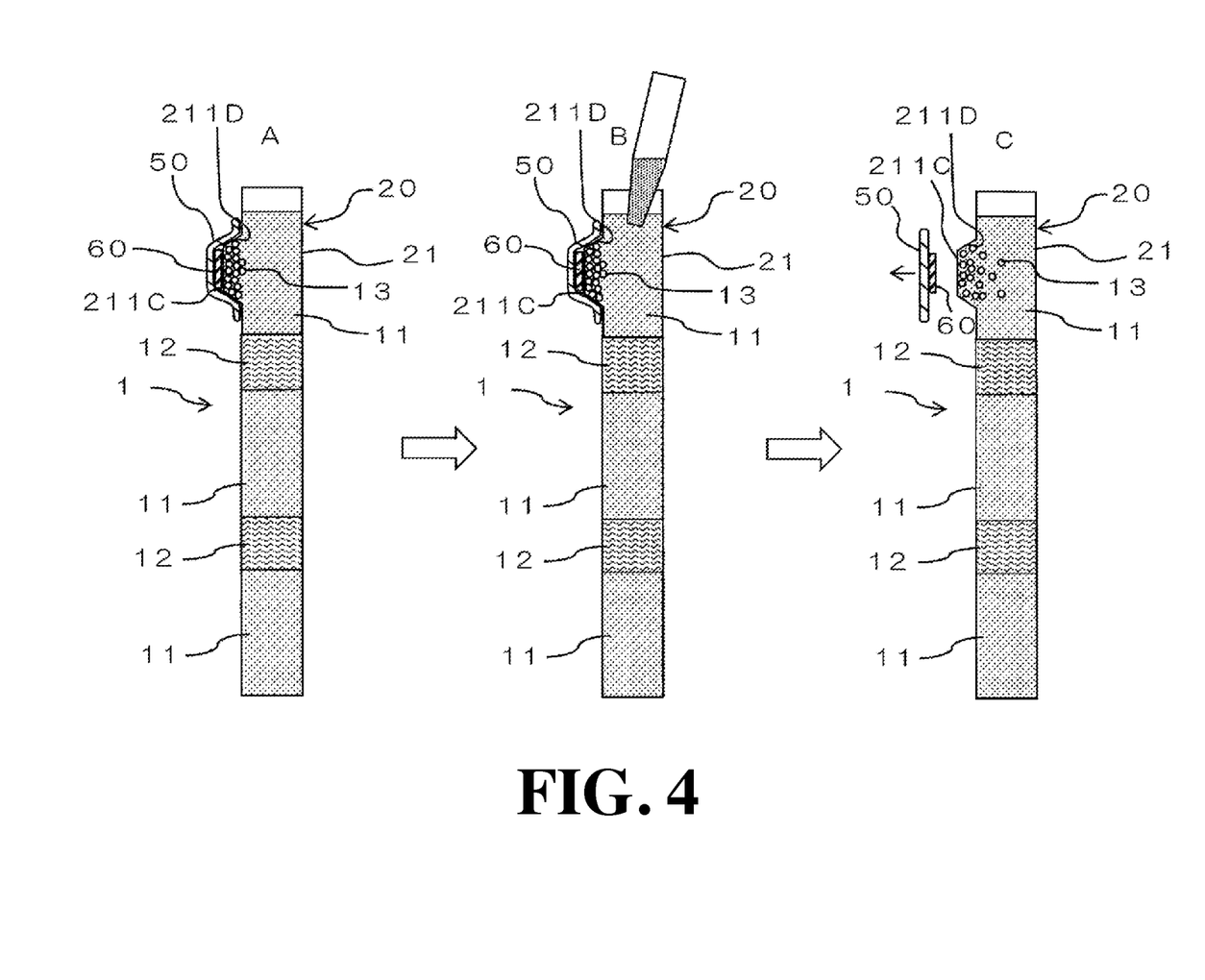
FIG. 4 is a schematic diagram for explaining a mode when operating the magnetic particles, and shows a state from when the magnetic particles are aggregated in the container to when the magnetic particles are dispersed in the container.
Figure 5:
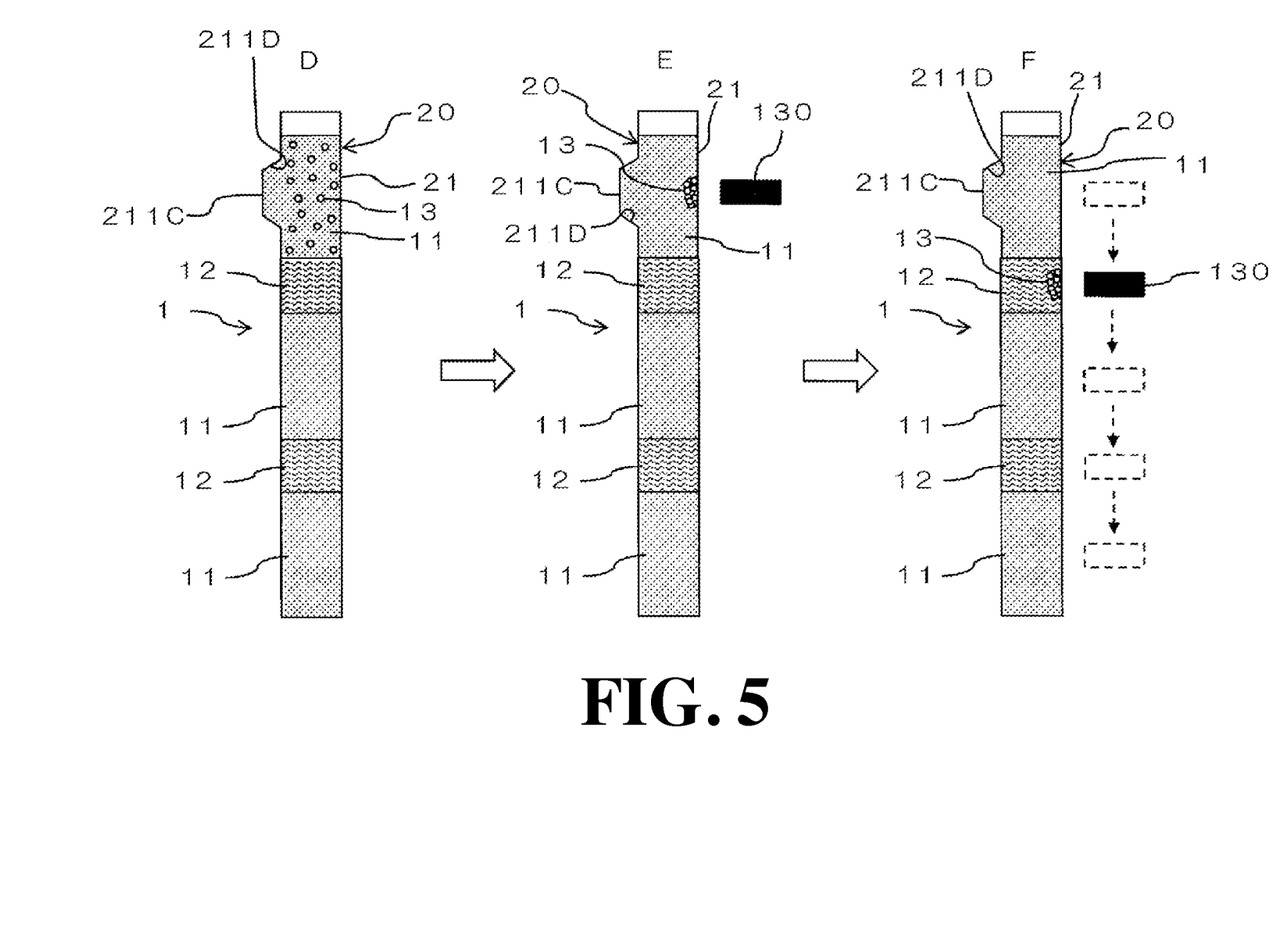
FIG. 5 is a schematic diagram for explaining a mode when operating the magnetic particles, and shows a state from when the magnetic particles are dispersed in the container to when the magnetic particles are moved below the container.

FIG. 4 is a schematic diagram for explaining a mode when operating the magnetic particles 13, and shows a state from when the magnetic particles 13 are aggregated in the container 20 to when the magnetic particles 13 are dispersed in the container 20. FIG. 5 is a schematic diagram for explaining a mode when operating the magnetic particles 13, and shows a state from when the magnetic particles 13 are dispersed in the container 20 to when the magnetic particles 13 are moved below the container 20.

Note that in FIG. 4 and FIG. 5, the shape of the device 1 (container 20) is simplified for easy understanding. Further note that FIG. 4 and FIG. 5 show a state in which the front side of the container 20 faces leftward and the rear surface side of the container 20 faces rightward.

"A" of FIG. 4, as described above, shows the device 1 in which a large number of magnetic particles 13 are contained in the liquid layer 11 (immobilization layer 11A) of the uppermost portion (bulging portion 21) of the container 20. In "A" of FIG. 4, as described above, the sealing member 50 is adhered to the outer surface of the protruding portion 211C of the container 20, so the holding magnet 60 is held outside the protruding portion 211C by the sealing member 50. Further, in the container 20, the magnetic particles 13 are aggregated in the recess 211D of the protruding portion 211C by the magnetic force of the holding magnet 60. That is, "A" of FIG. 4 shows a state in which the device 1 is stored, or a state in which the device 1 is taken out from the stored state.

From the state shown in "A" of FIG. 4, the operator removes the cap 30 (see FIG. 1) of the container 20 and introduces a liquid sample into the inside through the opening on the upper surface of the container 20 as shown in "B" of FIG. 4.

Further, as shown in "C" of FIG. 4, the operator pulls the sealing member 50 and peels the sealing member 50 from the protruding portion 211C of the container 20. As a result, together with the sealing member 50, the holding magnet 60 is separated from the container 20. As described above, the holding magnet 60 is attached to the container 20 by adhering the sealing member 50 to the container 20, and is detached (separated) from the container 20 by peeling the sealing member 50 from the container 20.

As a result, the magnetic force of the holding magnet 60 will become inactive at the bulging portion 21 of the container 20, and the magnetic particles 13 aggregated in the recess 211D of the protruding portion 211C will be dispersed in the bulging portion 21. As described above, the upper end portion and the lower end portion of the recess D are inclined. Therefore, the magnetic particles 13 are smoothly dispersed in the bulging portion 21 without remaining in the recess 211D.

And as shown in "D" of FIG. 5, when the magnetic particles 13 are dispersed in the entire region in the bulging portion 21, the target substance contained in the immobilization layer 11A is selectively immobilized to the magnetic particles 13.

Note that the operations shown in "A" to "C" of FIG. 4 and "D" of FIG. 5 to the device 1 may be performed before the device 1 is fixed to the apparatus 100, or may be performed in a state in which the device 1 is fixed to the apparatus 100. In the state shown in "E" and "F" of FIG. 5, the device 1 is fixed in the apparatus 100.

Thereafter, as shown in "E" of FIG. 5, the operation magnet 130 which is a magnetic force source is brought closer to the rear surface 212 of the bulging portion 21. The magnetic particles 13 to which the target substance is immobilized are collected on the operation magnet 130 side in the container 20 by the action of the magnetic field. As a result, the magnetic particles 13 are completely separated from the recess 211D and collected on the rear surface 212 side of the bulging portion 21. Then, as shown in "F" of FIG. 5, when the operation magnet 130 is moved in the longitudinal direction (up-down direction) of the container 20 along the outer peripheral surface of the container 20, following the change of the magnetic field, the magnetic particles 13 also move along the longitudinal direction of the container 20 and sequentially move through the alternately stacked liquid layer 11 and gel-like medium layer 12.

Then, when the operation magnet 130 is moved to a position facing the tip of the container 20, the magnetic particles 13 are moved to the eluting layer 11C. Thus, the target substance is eluted in the eluting layer 11C.

Thus, by dispersing the magnetic particles 13 in the liquid layer 11 and bringing the magnetic particles 13 into contact with the liquid in the liquid layer 11, immobilization of the target substance to the magnetic particles 13, a washing operation to remove the impurities attached to the surface of the magnetic particles 13, an operation to elute the target substance immobilized to the magnetic particles 13 into the liquid, etc., are performed.

At this time, the most of the liquid physically attached as droplets around the magnetic particles 13 is detached from the surfaces of the magnetic particles 13 when the magnetic particles 13 enter the gel-like medium layer 12. The gel-like medium layer 12 is perforated by the penetration of the magnetic particles 13 into the gel-like medium layer 12 and the movement of the magnetic particles 13 through the gel-like medium layer 12, but the holes in the gel-like medium layer 12 are immediately closed by the self-repairing action by the restoring force of the gel. Therefore, almost no liquid flows into the gel-like medium layer 12 through the through-holes formed by the magnetic particles 13.

The magnetic particles 13 are moved along the rear surface 212 of the bulging portion 21 and the rear surface of the straight portion 22 when moved in the container 20. That is, the magnetic particles 13 are moved along the flush portion of the container 20. For this reason, the magnetic particles 13 can be smoothly moved inside the container 20.

4. [Functions and Effects]

(1) According to this embodiment, as shown in FIG. 2, in the device 1, the holding magnet 60 is in contact with the outer surface of the bulging portion 21 (sample introduction space).

Therefore, during the storage of the device 1, the magnetic particles 13 in the bulging portion 21 (sample introduction space) 1 are aggregated and held at the position facing the holding magnet 60 in the sample introduction space by the magnetic force of the holding magnet 60.

Therefore, during the storage of the device 1, the magnetic particles 13 can be prevented from being brought into contact with the gel-like medium layer 12.

Further, when using the device 1, the magnetic particles 13 can be dispersed in the liquid layer 11 (immobilization layer 11A) by moving the holding magnet 60 away from the container 20. When the sample is introduced into the container 20 in this state, the sample and the magnetic particles 13 can be smoothly mixed in the liquid layer 11 (immobilization layer 11A). Thus, the target substance can be fixed to the magnetic particles 13.

As a result, a series of operations of mixing the magnetic particles 13 and the sample outside the device 1 and introducing the mixture (mixed solution) into the device 1 can be omitted. Further, the magnetic particles 13 are not brought into contact with the gel-like medium layer 12 during the storage, so almost all of the magnetic particles 13 can be used for separation/purification of the target substance.

Thus, according to this embodiment, the operation of the operator can be simplified, and generation of magnetic particles 13 that do not contribute to the separation/purification of the target substance can be suppressed.

(2) Further, according to this embodiment, as shown in FIG. 2, in the device 1, the recess 211D is formed on the inner surface of the bulging portion 21 (portion where the sample introduction space is formed) at the position facing the holding magnet 60.

Therefore, the magnetic particles 13 in the bulging portion 21 are aggregated on the inner side of the recess 211D formed on the inner surface of the bulging portion 21 by the magnetic force of the holding magnet 60.

As a result, the magnetic particles 13 can be held by the recess 211D of the bulging portion 21.

Therefore, during the storage of the device 1, the magnetic particles 13 can be stably held in the liquid layer 11 (immobilization layer 11A).

(3) Further, according to this embodiment, as shown in FIG. 2, in the device 1, the rear surface of the bulging portion 21 is formed as a flush-shaped opposing surface. In the device 1, the recess 211D is formed at a position different from the rear surface 212 of the bulging portion 21 and at a position facing the rear surface 212.

Therefore, as shown in FIG. 5, when the operation magnet 130 is moved along the container 20, it is possible to prevent the recess 211D from hindering the movement of the operation magnet 130.

Further, after the magnetic particles 13 are dispersed in the liquid layer 11 (immobilization layer 11A), the magnetic particles 13 can be separated from the recess 211D by the magnetic force of the operation magnet 130.

Therefore, when moving the operation magnet 130 along the container 20, it is possible to suppress the magnetic particles 13 from remaining in the recess 211D.

(4) Further, according to this embodiment, as shown in FIG. 2, in the device 1, the holding magnet 60 is arranged at a position lower than the liquid level of the liquid layer 11 (immobilization layer 11A) in the bulging portion 21 and at a position facing the protruding portion 211C.

Therefore, during the storage of the device 1, the magnetic particles 13 can be stably held in the liquid layer 11 (immobilization layer 11A).

As a result, during the storage of the device 1, the magnetic particles 13 can be prevented from being exposed to the outside of the liquid layer 11 (immobilization layer 11A) and dried.

(5) Further, according to this embodiment, as shown in FIG. 4, in the device 1, the holding magnet 60 is detachably attached to the container 20.

Therefore, by attaching the holding magnet 60 to the container 20, the magnetic particles 13 can be held in the liquid layer of the container 20 by the magnetic force of the holding magnet 60. Then, by removing the holding magnet 60 from the container 20, the magnetic particles 13 can be dispersed in the liquid layer 11 (immobilization layer 11A).

(6) In addition, according to this embodiment, as shown in FIG. 2, the holding magnet 60 is attached to the container 20 by the sealing member 50 adhered to the container 20.

Therefore, the holding magnet 60 can be attached to and detached from the container 20 with a simple configuration.

5. [Second Embodiment]

Hereinafter, using FIG. 6, the configuration of the magnetic particle operation device 1 according to a second embodiment of the present invention will be described. Note that the same reference numeral is allotted to the same configuration as that of the first embodiment, and the description thereof will be omitted.

Figure 6:
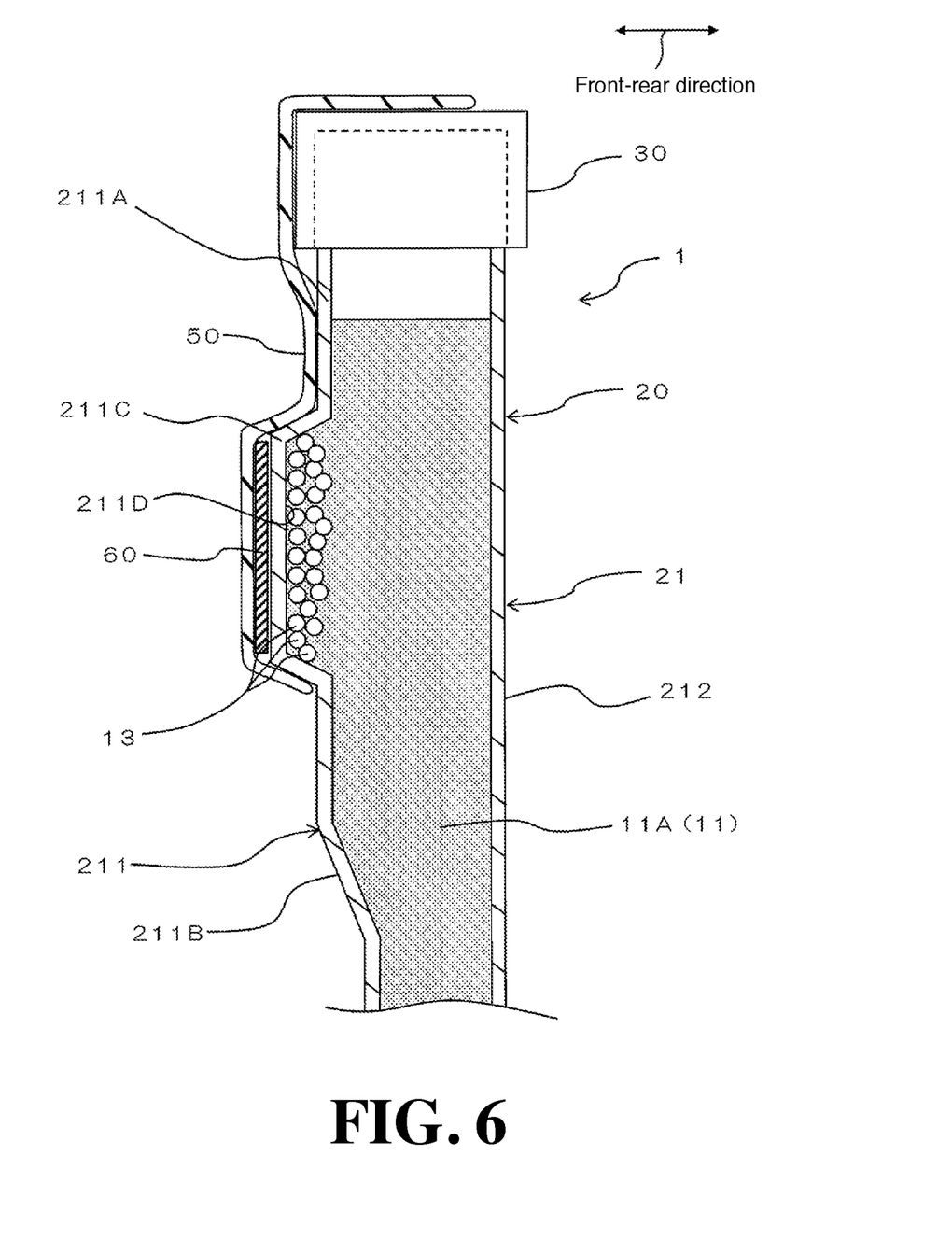
FIG. 6 is a cross-sectional view showing a configuration example of a magnetic particle operation device according to a second embodiment of the present invention.

FIG. 6 is a cross-sectional view showing a configuration example of a magnetic particle operation device 1 according to a second embodiment of the present invention.

In the above-described first embodiment, the sealing member 50 is adhered to the front surface 211 (vertical plane 211A) of the container 20 (bulging portion 21). On the other hand, in the second embodiment, the sealing member 50 is adhered to the container 20 and the cap 30.

Specifically, in the second embodiment, the sealing member 50 in the device 1 is also used as an unopened confirmation seal. The sealing member 50 is adhered to the vertical plane 211A of the container 20 with the holding magnet 60 interposed therebetween, and is adhered so as to cross the container 20 and the cap 30. One end portion of the sealing member 50 is adhered to the upper surface of the cap 30. The device 1 is stored in this state.

The operator confirms that the device 1 is unopened by confirming that the sealing member 50 is adhered so as to cross the container 20 and the cap 30.

When using device 1, the operator first removes the sealing member 50 from the container 20 in order to remove the cap 30 from the container 20 (in order to use the magnetic particle operation device 1).

As a result, together with the sealing member 50, the holding magnet 60 is separated from the container 20. And in the container 20, the magnetic particles 13 are dispersed.

As described above, according to the device 1 of the second embodiment, when the operator performs an operation of removing the sealing member 50 in order to remove the cap 30 from the container 20 (in order to use the magnetic particle operation device 1), the holding magnet 60 is separated (detached) from the container 20 along with the operation. In other words, the operator can separate the holding magnet 60 from the container 20 by performing the operation of removing the unopened confirmation seal, which is a normal operation for using the magnetic particle operation device 1.

Therefore, a series of operations for separating the holding magnet 60 from the container 20 can be simplified.

6. Modified Embodiment

In the above-described embodiments, it is described that the straight portion 22 of the container 20 is provided with the cleaning layer 11B and the eluting layer 11C as the liquid layer 11. However, in the container 20, the straight portion 22 may be provided with a reaction layer for causing a predetermined reaction with respect to the target object. Further, in the bulging portion 21 and the straight portion 22, the liquid layer 11 and the gel-like medium layer 12 may be stacked in three layers. Furthermore, the liquid portion 11 and the gel-like medium layer 12 may be stacked in three layers in the straight portion 22. For example, in the container 20, the bulging portion 21 may be filled with an immobilization layer 11A, and the straight portion 22 may be filled with a gel-like medium layer 12 and an eluting layer 11C. In this case, in the straight portion 22, the gel-like medium layer 12 is positioned on the upper side and the eluting layer 11C is positioned on the lower side.

In the above-described embodiment, the holding magnet 60 is described as a permanent magnet. However, the holding magnet 60 may be an electric magnet.

Further, in the above-described embodiment, the holding magnet 60 is described as being held in contact with the outer surface of the bulging portion 21. However, the holding magnet 60 may be held in a state of being close to the outer surface of the bulging portion 21. For example, the holding magnet 60 may be fixed to a storage container for storing the device 1 and the holding magnet 60 may be close to the bulging portion 21 in a state in which the device 1 is stored in the storage container.

Further, in the above-described embodiment, the holding magnet 60 is described as being attached to the container 20 by the sealing member 50. However, the holding magnet 60 may be attached to the container 20 by a configuration other than the sealing member 50. For example, the holding magnet 60 or a member holding the holding magnet 60 is provided with an engaging portion, an engaged portion is provided on the outer surface of the bulging portion 21, and the holding magnet 60 may be detachably attached to the container 20 by engaging the engaging portion and the engaged portion.

DESCRIPTION OF REFERENCE SYMBOLS 1 magnetic particle operation device
11 liquid layer
11A immobilization layer
11B cleaning layer
11C eluting layer
12 gel-like medium layer
13 magnetic particles
20 container
21 bulging portion
22 straight portion
30 cap
50 sealing member
60 holding magnet
130 operation magnet
211C protruding portion
211D recess
212 rear surface

The invention claimed is:

1. A magnetic particle operation device comprising:
a tubular container having a longitudinal shape and including
a sample introduction space accommodating magnetic particles in which a target substance is immobilized to the magnetic particles, the target substance being included in a sample to be received from outside of the tubular container, the sample introduction space having a protruding portion with a recessed portion formed on an inner surface of the protruding portion within the tubular container, and
a sample movement space in which a gel-like medium layer and a liquid layer are alternately arranged in a longitudinal direction of the sample movement space;
a first magnet detachably attached to an outer surface of the protruding portion of the tubular container to face the sample introduction space, the first magnet configured to apply a first magnetic force to the magnetic particles, thereby holding the magnetic particles in the sample introduction space in the tubular container, and
a second magnet provided outside the tubular container to face the container, and longitudinally movable along the container, the second magnet configured to apply a second magnetic force to the magnetic particles, thereby moving the magnetic particles from the sample introduction space to the sample movement space, passing through the gel-like medium layer and the liquid layer in the longitudinal direction.

2. The magnetic particle operation device as recited in claim 1,
wherein the first magnet is arranged at a position lower than a liquid level of the liquid in the sample introduction space.

3. The magnetic particle operation device as recited in claim 1,
wherein the first magnet is detachably attached to the tubular container via a sealing member adhered to the tubular container.

4. The magnetic particle operation device as recited in claim 3,
wherein the tubular container includes a main body which defines the sample introduction space and the sample movement space, and a cap detachably attached to the main body to open and close the sample introduction space, and wherein the sealing member is adhered so as to cross the main body and the cap.

5. The magnetic particle operation device as recited in claim 3,
wherein when viewed in a cross-sectional view while the sealing member is attached to the protruding portion, and the sealing member includes a side surface, a top surface, and a bottom surface, the top surface and the bottom surface of the sealing member extending in a direction oblique to the side surface of the sealing member, and
wherein when the sealing member is attached to the protruding portion, and the first magnet is disposed between a side surface of the protruding portion and the side surface of the sealing member.

6. The magnetic particle operation device as recited in claim 1,
wherein the sample introduction space is provided at an uppermost portion of the tubular container.

7. The magnetic particle operation device as recited in claim 1,
wherein when viewed in a cross-sectional view, the protruding portion includes a side surface, a top surface, and a bottom surface, the top surface and the bottom surface of the protruding portion extending in a direction oblique to the side surface of the protruding portion.

* * * * *